United States Patent
Grayson et al.

(10) Patent No.: US 9,535,025 B2
(45) Date of Patent: Jan. 3, 2017

(54) PROBE ASSEMBLY AND METHOD FOR CONTACTLESS ELECTRICAL CHARACTERIZATION OF BURIED CONDUCTING LAYERS

(71) Applicant: Northwestern University, Evanston, IL (US)

(72) Inventors: Matthew Grayson, Evanston, IL (US); Wang Zhou, Evanston, IL (US); Gautham Badri Ramachandran Sundar, Evanston, IL (US)

(73) Assignee: Northwestern University, Evanston, IL (US)

( * ) Notice: Subject to any disclaimer, the term of this patent is extended or adjusted under 35 U.S.C. 154(b) by 313 days.

(21) Appl. No.: 14/382,599

(22) PCT Filed: Mar. 6, 2013

(86) PCT No.: PCT/US2013/029438
§ 371 (c)(1),
(2) Date: Sep. 3, 2014

(87) PCT Pub. No.: WO2013/134422
PCT Pub. Date: Sep. 12, 2013

(65) Prior Publication Data
US 2015/0022223 A1   Jan. 22, 2015

Related U.S. Application Data

(60) Provisional application No. 61/607,384, filed on Mar. 6, 2012.

(51) Int. Cl.
*G01N 27/22*   (2006.01)
*G01R 1/07*   (2006.01)
*G01R 31/312*   (2006.01)

(52) U.S. Cl.
CPC .......... *G01N 27/22* (2013.01); *G01R 1/07* (2013.01); *G01R 31/312* (2013.01)

(58) Field of Classification Search
USPC ............. 324/663, 658, 649, 600, 149, 601, 686,324/243, 425, 511, 537, 679, 713, 750.25,324/754.03, 762.01, 750.01–750.3, 754.01,324/754.05–754.06, 696, 719; 438/17, 151, 438/196, 400; 257/E21.002, 330, E21.422, 257/E21.531, E23.179, E27.016, E29.166, 254, 257/296; 73/862.626, 31.06, 514.32
See application file for complete search history.

(56) References Cited

U.S. PATENT DOCUMENTS

2006/0087327 A1   4/2006   Ueno et al.
2006/0279297 A1   12/2006   Nystrom et al.
(Continued)

FOREIGN PATENT DOCUMENTS

KR   20040042420 A   5/2004
KR   20110112432 A   10/2011

OTHER PUBLICATIONS

International Search Report from PCT/US2013/029438, mailing date Jun. 27, 2013.

*Primary Examiner* — Melissa Koval
*Assistant Examiner* — Nasima Monsur
(74) *Attorney, Agent, or Firm* — Klintworth & Rozenblat IP LLC (57) ABSTRACT

A probe assembly includes plural capacitive contacts that are separate from each other and a conductive depletion gate disposed between and separating the contacts from each other. The depletion gate is configured to receive a direct electric voltage to deplete regions of a sample under test of electrons. The contacts are configured to be placed in close proximity to a buried conducting layer in the sample under (Continued)

test without engaging the buried conducting layer, thereby capacitively coupling to the buried conducting layer. A first subset of the capacitive contacts is configured to apply an alternating electric current to a portion of the sample under test and a second subset of the capacitive contacts is configured to sense an alternating voltage response of the portion of the sample under test to characterize one or more electrical properties of the sample under test without the capacitive contact with the buried conductive layer.

20 Claims, 4 Drawing Sheets

(56) References Cited

U.S. PATENT DOCUMENTS

2009/0055977 A1    2/2009  Burke
2012/0146669 A1*   6/2012  Erickson .............. G01R 31/312
                                                           324/683

\* cited by examiner

PROBE ASSEMBLY AND METHOD FOR CONTACTLESS ELECTRICAL CHARACTERIZATION OF BURIED CONDUCTING LAYERS

CROSS-REFERENCE TO RELATED APPLICATIONS

This application claims priority to U.S. Provisional Application No. 61/607,384, which was filed on 6 Mar. 2012, and the entire disclosure of which is incorporated by reference.

STATEMENT REGARDING FEDERALLY SPONSORED RESEARCH & DEVELOPMENT

This invention was made with government support under DMR0520513 awarded by the National Science Foundation and DMR0748856 awarded by the National Science Foundation. The government has certain rights in the invention.

BACKGROUND

A probe assembly and/or method for characterizing electrical conductivity of a conducting layer that is buried below an insulating layer, such as in transistor substrates in semiconductor industry, is provided herein. Alternatively, one or more embodiments described herein may be used for other types of substrates or devices.

Diffused metal contacts are used for some known four-point electrical characterization methods for buried (e.g., not exposed) conducting layers. These methods, however, may require the use of alloyed ohmic contacts with the buried conducting layers, which can be problematic. Such ohmic contacts may be problematic in low-density systems (e.g., samples under test or examination that have relatively low carrier density in a semiconductor body or layer in which the buried conducting layer is disposed) and can take considerable time to fabricate. Additionally, such contacts may require different alloy recipes for the ohmic contacts used in n- and p-type doped systems (e.g., n- and p-type doped semiconductor or insulator samples). For some relatively new materials (e.g., recently developed materials) used in the samples having the buried conducting layers, the recipes for creating alloy recipes for the ohmic contacts may have not yet been developed yet. Moreover, alloyed ohmic contacts can be permanent such that, once a sample is used for characterization purposes, the sample cannot be reused. The sample may be destroyed or otherwise altered in such a manner to provide the ohmic contacts with the buried conducting layer that the sample may not be able to be reused for one or more other (e.g., intended) purposes.

Some known probe stations can be used for four-point electrical characterization methods of semiconductor or nonconducting samples having the buried conducting layers, but these stations may require pre-fabrication processing of the sample in order to expose the buried conducting layer engagement with the probes of the station. Additionally, the sample may not be reused after characterization due to scratching of the sample with the probes during examination of the sample. Moreover, the probes can eventually wear down due to the repeated physical contact with the samples.

BRIEF DESCRIPTION

In an embodiment, a probe assembly includes plural capacitive contacts that are separate from each other and a conductive depletion gate disposed between and separating the contacts from each other. The term "capacitive contact" refers to a conductive body that can be capacitively coupled with another conductive body, such as a buried conducting layer in a semiconductor or insulator body, with at least a portion of a semiconductor or insulator body disposed between the conductive body of the capacitive contact and the buried conducting layer. The capacitive contact need not necessarily be a capacitor itself or include a capacitor.

The depletion gate is configured to receive a direct electric voltage in order to deplete regions of a sample under test of electrons. The sample under test may include a semiconductor or insulator body having a buried conducting layer. The contacts are configured to be placed in close proximity to the buried conducting layer in the sample under test without directly engaging the buried conducting layer, but rather capacitively coupling to the buried conducting layer. For example, and as described in more detail below, the contacts may be positioned close to the buried conducting layer, but without contacting, abutting, or otherwise engaging the sample under test. Optionally, the contacts may abut, contact, or otherwise engage the semiconductor or insulator body without abutting, contacting, or otherwise engaging the buried conducting layer. A first subset of the capacitive contacts is configured to apply an alternating electric current to a portion of the sample under test and a second subset of the capacitive contacts is configured to sense an alternating voltage response of the portion of the sample under test in order to characterize one or more electrical properties of the sample under test without the capacitive contacts having ohmic contact with the buried conducting layer.

In an embodiment, a method includes positioning a probe assembly in close proximity to a buried conducting layer in a sample under test. The sample under test includes a semiconductor or insulator body with the buried conducting layer. The probe assembly has plural capacitive contacts that are separate from each other and a conductive depletion gate disposed between and separating the capacitive contacts from each other. The method also includes supplying the depletion gate with a direct electric voltage in order to deplete regions of the sample under test of electrons, conducting an alternating electric current through a first subset of the capacitive contacts to a portion of the sample under test, and sensing an alternating voltage response of the portion of the sample under test in response to the alternating electric current being conducted through the first subset of the capacitive contacts in order to characterize one or more electrical properties of the sample under test without the capacitive contacts having ohmic contact with the buried conducting layer.

In an embodiment, a probe assembly includes capacitive contacts separated from each other and arranged around a region under test. The contacts are configured to be positioned proximate to a sample under test and thereby capacitively couple to the buried conducting layer. The sample under test includes a semiconductor or insulator body having a buried conducting layer. The capacitive contacts are configured to be positioned proximate to the sample under test without contacting the buried conducting layer. A first subset of the capacitive contacts is configured to inject an alternating current into the sample under test outside of a portion of the sample under test that faces the region under test between the capacitive contacts. A different, second subset of the capacitive contacts is configured to sense a voltage response of the portion of the sample under test in response to the alternating current being injected into the sample under test. The voltage response is indicative of at least one of a charge carrier mobility or a charge carrier density in the portion of the sample under test that faces the region under test.

BRIEF DESCRIPTION OF THE DRAWINGS

The present inventive subject matter will be better understood from reading the following description of non-limiting embodiments, with reference to the attached drawings.

DETAILED DESCRIPTION

As used herein, an element or step recited in the singular and proceeded with the word "a" or "an" should be understood as not excluding plural of said elements or steps, unless such exclusion is explicitly stated. Furthermore, references to "one embodiment" of the presently described subject matter are not intended to be interpreted as excluding the existence of additional embodiments that also incorporate the recited features. Moreover, unless explicitly stated to the contrary, embodiments "comprising," "comprises," "including," "includes," "having," or "has" an element or a plurality of elements having a particular property may include additional such elements not having that property. Additionally, values of variables, coefficients, and the like are not intended to be limiting on all embodiments of the presently described inventive subject matter. In at least one embodiment, one or more different values may be used.

In accordance with one embodiment, a probe assembly includes a contactless proximity probe that electrically characterizes buried conducting films, with little to no sample processing (e.g., preparation for characterization) and/or without the need for ohmic contacts with the buried conducting films. The probe may be simply placed in proximity or in direct contact with a sample of interest (also referred to as a sample under test or under examination) having a semiconductor body with a buried conducting layer. As used herein, the term "contactless" means that the probe does not engage, abut, or otherwise directly and physically contact the buried conducting films of the samples or conductive bodies that are conductively coupled with the buried conducting films. The probe may be located "proximate" to the sample under test such as by engaging, abutting, or otherwise directly and physically contacting the sample without being conductively coupled with the films. Additional manners to determine whether the probe is proximate to the sample under test are described below. Also as used herein, "buried" means that the referenced object (e.g., the conducting film of a buried conductive film) may not normally or typically be exposed or visible (e.g., using the visible wavelengths of light or to the naked eye) to an observer located outside of the sample that contains the buried object. For example, the probe can provide for non-invasive examination or characterization of buried conducting films without damaging the samples or bodies that contain the films, exposing the films, and the like.

With the proximity probe, a user can perform a four-point conductance measurement of a buried conducting layer or film via AC capacitive coupling (in one embodiment), and the measured sample is untouched and can be reused for processing in a future device that includes the sample. With an external magnetic field applied to the sample, a user of the probe can determine the carrier density and electrical mobility of carriers in the sample.

Figure 1:
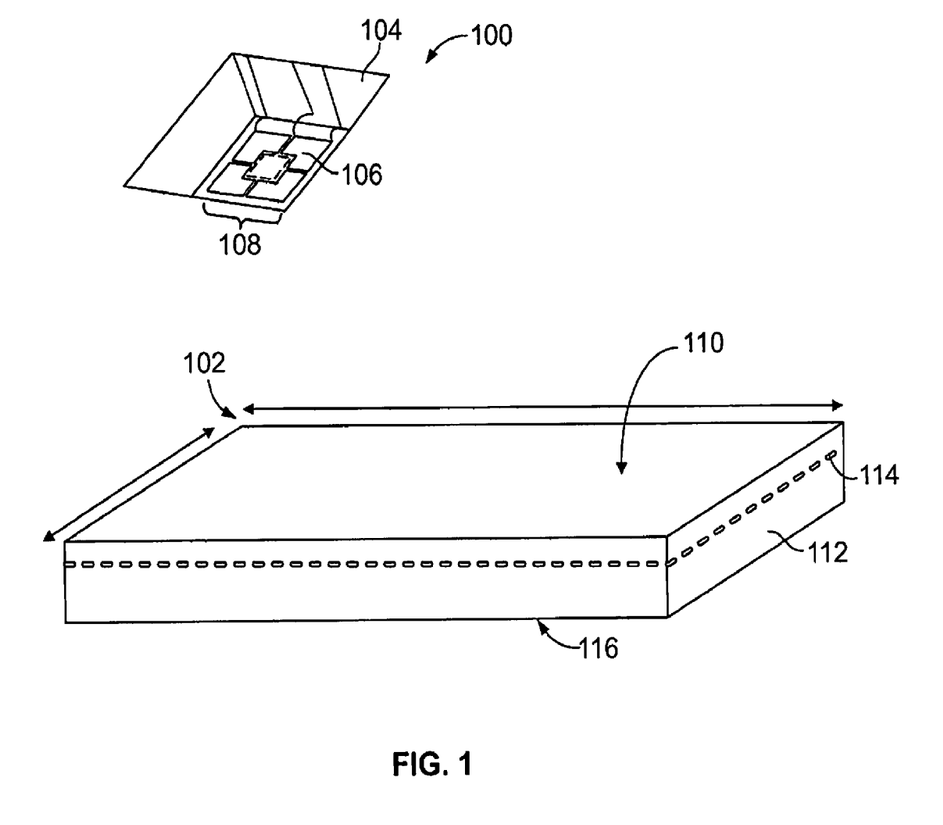
FIG. 1 is a perspective view of an embodiment of a contactless probe assembly and a portion of a sample under test.

FIG. 1 is a perspective view of an embodiment of a contactless probe assembly 100 and a portion of a sample under test 102. The probe assembly 100 includes a supporting body 104 and several capacitive contacts 106 in a sample overlay 108, which represents a portion of the probe assembly 100 that is disposed at or near the sample under test 102. During examination or testing of the sample under test 102, the overlay 108 part of the probe assembly 100 can be placed onto the sample under test 102, such as by placing the overlay 108 and capacitive contacts 106 in direct, abutting contact with an exposed surface 110 of the sample under test 102. Additionally or alternatively, the overlay 108 and capacitive contacts 106 may be placed relatively close to, but not in contact with, the exposed surface 110 of the sample under test 102, as described in more detail below.

The sample under test 102 may be a semiconductive or insulating body 112 with a conductive or conducting layer 114 disposed within the semiconductor or insulator body 112. The conducting layer 114 may be referred to as a buried conducting layer in that the layer 114 may be disposed between the exposed surface 110 of the semiconductor or insulator body 112 and an opposite surface or side 116 of the semiconductor or insulator body 112. The buried conducting layer 114 may not be exposed on either surface or side 110, 116 such that the four point characterization method that uses ohmic contacts may not be used without removing one or more portions of the semiconductor or insulator body 112 to expose more of the buried conducting layer 114.

Only a relatively small portion of the sample under test 102 is shown in FIG. 1. The surface area of the exposed surface 110 of the sample under test 102 may be much larger than the surface area of the overlay 108 of the probe assembly 100. For example, the overlay 108 of the probe assembly 100 may be sufficiently small that one or more of the probe assembly 100 and/or the sample under test 102 may be moved relative to the other during characterization of the sample under test 102 by the probe assembly 100. The probe assembly 100 may collect measurements that characterize the sample under test 102 (as described below) as the probe assembly 100 moves over different portions of the sample under test 102 (and/or the sample under test 102 moves relative to the probe assembly 100).

Figure 2:
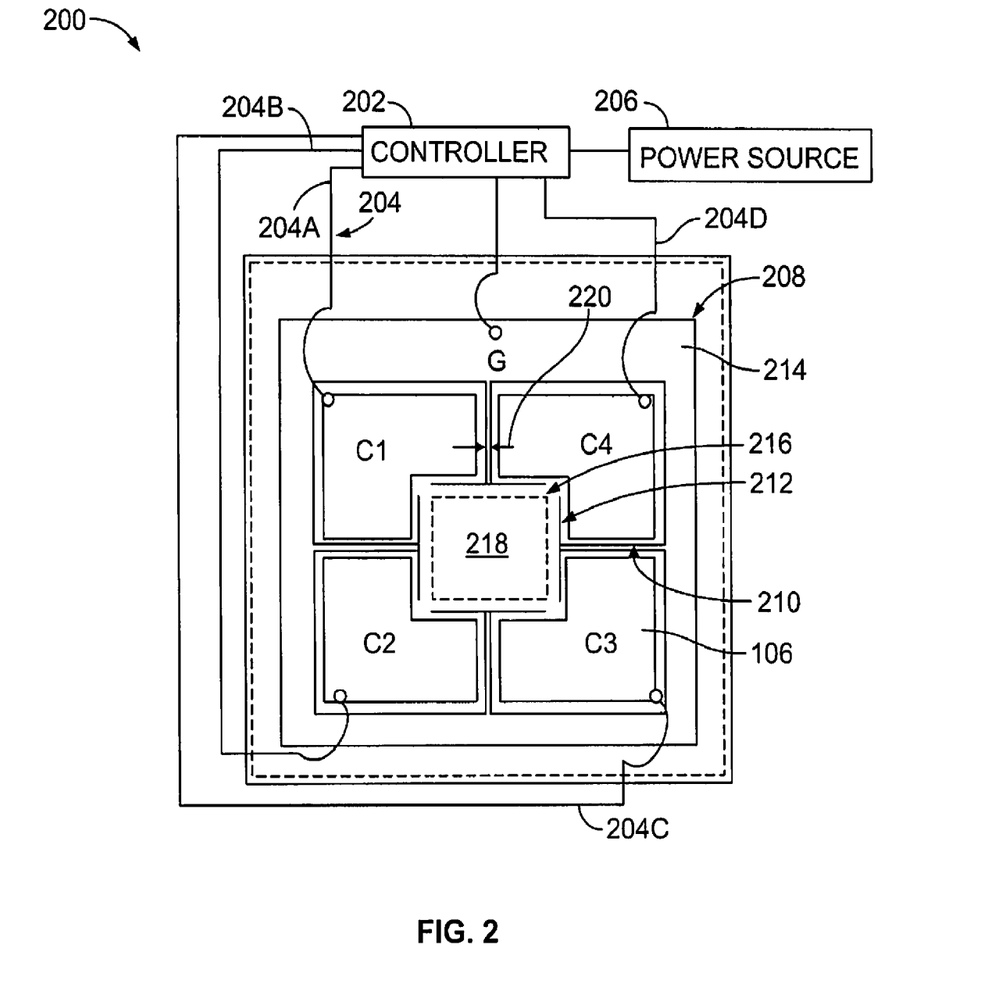
FIG. 2 schematically illustrates an example of a characterization system that includes the probe assembly shown in FIG. 1.

FIG. 2 schematically illustrates a characterization system 200 that includes the probe assembly 100. Although only the overlay 108 of the probe assembly 100 is shown in FIG. 2, the overlay 108 may represent the probe assembly 100. The probe assembly 100 includes the capacitive contacts 106, which are labeled as C1 through C4 in FIG. 2. Although four capacitive contacts C1-C4 are shown in FIG. 2, alternatively, a different number and/or arrangement of the capacitive contacts may be used.

The capacitive contacts C1-C4 are electrically insulated from each other. For example, the capacitive contacts C1-C4 are not conductively coupled, such as by a conductive body (e.g., bus). The capacitive contacts C1-C4 are conductively coupled with a controller 202 of the system 200 that controls operations of the capacitive contacts C1-C4. The capacitive contacts C1-C4 are conductively coupled with one or more conductive bodies 204 (e.g., bodies 204A-D), such as wires, busses, and the like. Although the conductive bodies 204 are shown coupled to the capacitive contacts C1-C4 on the side of the probe assembly 100 that faces the sample under test 102 and that may abut the exposed surface 110 (shown in FIG. 1) of the sample under test 102, the conductive bodies 204 may be connected with the capacitive contacts C1-C4 in another manner, such as behind the sides of the conductive bodies 204 that face the exposed surface 110 of the sample under test 102 during examination, to the sides of the capacitive contacts C1-C4, or in another location that does not interfere with the testing of the sample under test 102 by the probe assembly 100. For example, the conductive bodies 204 may be positioned elsewhere so that the bodies 204 are not positioned between the capacitive contacts C1-C4 and the exposed surface 110 of the sample under test 102.

The controller 202 can represent one or more processors, microcontrollers, or other circuitry components, that perform testing operations of the sample under test 102 (shown in FIG. 1). The controller 202 is conductively coupled with the capacitive contacts C1-C4 by the conductive bodies 204. As shown in FIG. 2, the conductive bodies 204 provide separate conductive pathways between each respective contact C1-C4 and the controller 202 such that the capacitive contacts C1-C4 are not conductively coupled. The circuitry within the controller 202 may maintain the separation of the capacitive contacts C1-C4 such that the capacitive contacts C1-C4 are not conductively coupled outside or inside the controller 202.

As described below, the controller 202 controls the supply of alternating electric current to some of the capacitive contacts C1-C4 and measures electrical characteristics (e.g., induced voltages) of the sample under test 102 using others of the capacitive contacts C1-C4. Although the description focuses on supplying alternating current to a group of certain capacitive contacts C1-C4 and measuring electrical characteristics using a group of certain other capacitive contacts C1-C4, alternatively other sets or groups of the capacitive contacts C1-C4 may be used to supply electric current to the sample under test 102 and/or measure the electrical characteristics of the sample under test 102. The controller 202 controls the supply of alternating electric current to one or more of the capacitive contacts C1-C4 from a power source 206, such as a source of alternating current (AC). The power source 206 can represent one or more sources of electric current.

The probe assembly 100 includes a conductive proximity depletion gate 208 (also referred to as "G" in FIG. 2) in the overlay 108. The gate 208 is conductively coupled with the controller 202 by a conductive body 204. The illustrated gate 208 includes an outer periphery portion 214 that continuously extends around the outer periphery of the capacitive contacts C1-C4. The periphery portion 214 is a single continuous conductive body in the illustrated embodiment. Alternatively, the periphery portion 214 may be segmented into separate conductive portions. The gate 208 also includes conductive separation fingers 210 disposed between the capacitive contacts C1-C4. The separation fingers 210 include lateral extensions 212 that are joined to ends of the separation fingers 210 and are elongated in opposite directions from the ends of the separation fingers 210. In the illustrated embodiment, the separation fingers 210 and lateral extensions 212 are all conductively coupled with each other by the periphery portion 214 as a single conductive body. Alternatively, one or more of the separation fingers 210, lateral extensions 212, and periphery portion 214 of the gate 208 may be separate from each other. In another embodiment, the periphery portion 214 of the gate 208 may not be provided in the probe assembly 100. For example, the gate 208 may include the separation fingers 210 and the lateral extensions 212 that are conductively coupled with the controller 208 by one or more conductive bodies 204, but may not include the periphery portion 214.

The separation fingers 210 of the gate 208 are disposed between adjacent or neighboring pairs of the capacitive contacts C1-C4. For example, a first elongated separation finger 210 is disposed between the capacitive contacts C1 and C2, a second elongated separation finger 210 is disposed between the capacitive contacts C2 and C3, a third elongated separation finger 210 is disposed between the capacitive contacts C3 and C4, and a fourth elongated separation finger 210 is disposed between the capacitive contacts C4 and C1. Additionally or alternatively, a different number and/or arrangement of the separation fingers 210 may be used.

Figure 3:
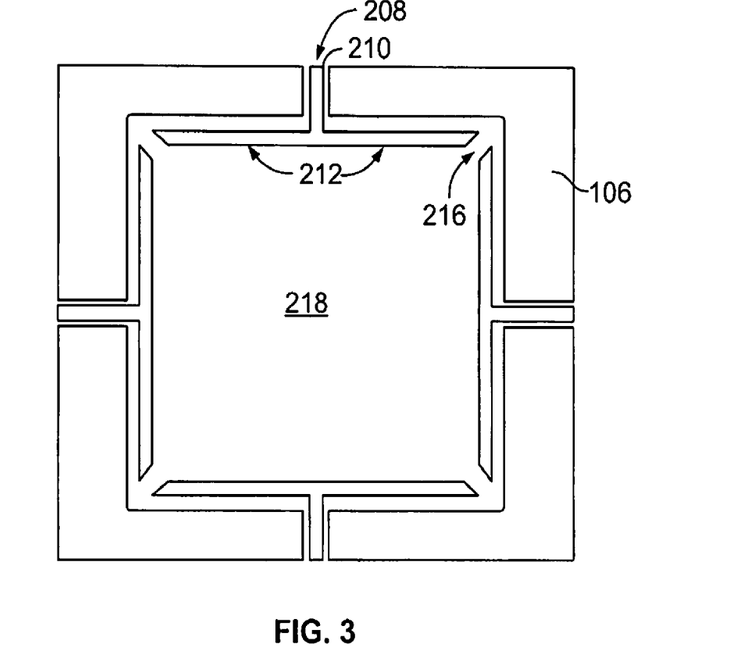
FIG. 3 illustrates a magnified view of a central portion of one example of a depletion gate shown in FIG. 2 that includes portions of separation fingers and lateral extensions of the gate (as also shown in FIG. 2).

With continued reference to FIG. 2, FIG. 3 illustrates a view of a portion of one example of the gate 208 that includes portions of the separation fingers 210 and the lateral extensions 212. The lateral extensions 212 of the gate 208 laterally extend in opposite directions from the respective separation fingers 210 to which the lateral extensions 212 are joined. The lateral extensions 212 extend from the separation fingers 210 toward the capacitive contacts C1-C4 that are separated by the separation fingers 210. For example, the lateral extensions 212 joined to the separation finger 210 disposed between the capacitive contacts C1 and C2 extend from the separation finger 210 to the contact C1 and to the contact C2. The lateral extensions 212 joined to the separation finger 210 disposed between the capacitive contacts C2 and C3 extend from the separation finger 210 to the contact C2 and to the contact C3. The lateral extensions 212 joined to the separation finger 210 disposed between the capacitive contacts C3 and C4 extend from the separation finger 210 to the contact C3 and to the contact C4. The lateral extensions 212 joined to the separation finger 210 disposed between the capacitive contacts C4 and C1 extend from the separation finger 210 to the contact C4 and to the contact C1.

The lateral extensions 212 extend toward different ones of the capacitive contacts C1-C4 without engaging or being coupled with the capacitive contacts C1-C4. The lateral extensions 212 that extend toward the same contact C1-C4 do not engage each other or the same contact C1-C4 such that an opening 216 is disposed between the lateral extensions 212. For example, a first opening 216 may be disposed between the lateral extensions 212 that extend toward the contact C1, a second opening 216 may be disposed between the lateral extensions 212 that extend toward the contact C2, a third opening 216 may be disposed between the lateral extensions 212 that extend toward the contact C3, and a fourth opening 216 may be disposed between the lateral extensions 212 that extend toward the contact C4.

The lateral extensions 212 and capacitive contacts C1-C4 extend around and define a region under test 218. The region under test 218 also may be referred to as a region under examination. The region under test 218 represents an area of the overlay 108 that corresponds with the portion of the sample under test 102 that is being examined by the characterization system 200. For example, when the probe assembly 100 is placed on or in close proximity to the sample under test 102, the portion of the sample under test 102 that faces or opposes the region under test 218 may be the portion of the sample under test 102 that is examined by the system 200. As described above, the probe assembly 100 and/or sample under test 102 may be moved relative to the other so that the region under test 218 extends over different portions of the sample under test 102. The portion of the buried conducting layer 114 within the semiconductor or insulator body 112 of the sample under test 102 that opposes the region under test 218 and that is located under the exposed surface 110 of the body 112 is the portion that is examined by the system 200. This portion represents an undepleted region of the semiconductor or insulator body 112, such as a portion that is not depleted of electrons or that has sufficient electrons to allow current to be conducted through the portion of the body 112 when current is applied through one or more of the capacitive contacts C1-C4. As described below, electrical characteristics of this portion of the body 112 are measured by the system 200.

Figure 4:
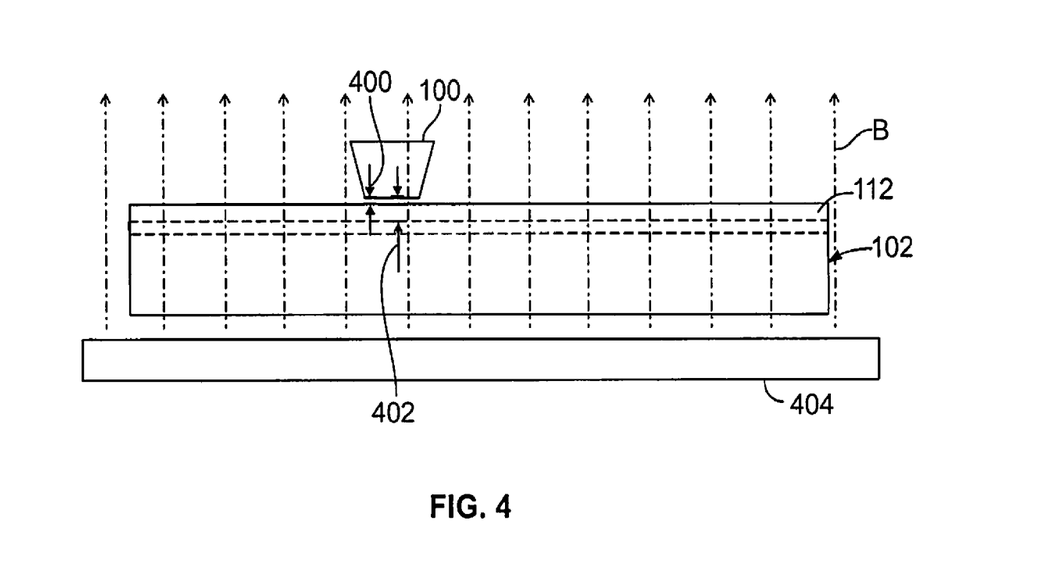
FIG. 4 illustrates a side view of an example of the probe assembly and the sample under test shown in FIG. 1.

With continued reference to the characterization system 200 shown in FIG. 2, FIG. 4 illustrates a side view of the probe assembly 100 and the sample under test 102 in accordance with one example. In operation, the probe assembly 100 is brought into close proximity to the sample under test 102. For example, the probe assembly 100 may be positioned in direct contact with the exposed surface 110 of the sample under test 102 or separated from the exposed surface 110 by a relatively small separation distance 400. The probe assembly 100 may engage the exposed surface 110 of the sample under test 102 such that the capacitive contacts C1-C4 and the gate 208 abut, contact, or otherwise engage the exposed surface 110 of the sample under test 102. With respect to the probe assembly 100 being positioned near the exposed surface 110 of the sample under test 102 without engaging, abutting, or contacting the exposed surface 110, the probe assembly may be positioned such that the capacitive contacts C1-C4 and the gate 208 are separated from the exposed surface 110 of the sample under test 102 by the separation distance 400 that is no more than five microns (or another relatively small distance, like a single micron).

In an embodiment, the separation distance 400 that may be used to characterize electrical characteristics of the sample under test 102 is limited by a width dimension 220 (shown in FIG. 2) of the separation fingers 210 of the gate 208. For example, the separation distance 400 may be limited such that a total distance 402 from the capacitive contacts C1-C4 to the buried conducting layer 114 in the sample under test 102 is no greater than the width dimension 220 of the separation fingers 210 of the gate 208.

The probe assembly 100 may be used to measure two or more electrical characteristics of the sample under test 102, such as the sheet resistance ($R_S$) and the Hall resistance ($R_H$). To measure the sheet resistance, the probe assembly 100 is brought into contact or close proximity with the sample under test 102 (as described above). The controller 202 directs one or more power sources 206 to supply a negative voltage to the gate 208 via one or more of the conductive bodies 204. This voltage may be a direct voltage. The negative voltage may be sufficiently large such that electrons in portions of the buried conducting layer 114 that face the gate 208 are depleted within the semiconductor or insulator body 112 of the sample under test 102 underneath the gate 208. The electrons may be depleted in regions of the buried conducting layer 114 that are opposite the outer periphery portion 214, the separation fingers 210, and/or the lateral extensions 212 of the gate 208.

The controller 202 supplies alternating electric current to a first subset of the capacitive contacts C1-C4 and measures the alternating voltage response, or induced voltage, in a second, different subset of the capacitive contacts C1-C4. The first subset of capacitive contacts C1-C4 through which the current is supplied may be referred to as a longitudinal supply subset of the capacitive contacts C1-C4 and the second subset of capacitive contacts C1-C4 through which the voltage response is measured may be referred to as a longitudinal sensing subset of the capacitive contacts C1-C4. The capacitive contacts C1-C4 in the longitudinal supply subset may be neighboring or adjacent capacitive contacts, such as the capacitive contacts C1 and C2. The capacitive contacts C1-C4 in the longitudinal sensing subset may be the other neighboring or adjacent capacitive contacts, such as the capacitive contacts C3-C4. Alternatively, other pairs of adjacent or neighboring capacitive contacts C1-C4 may be included in the supply and longitudinal sensing subsets, such as the capacitive contacts C2 and C3 in the longitudinal supply subset and the capacitive contacts C1 and C4 in the longitudinal sensing subset, the capacitive contacts C3 and C4 in the longitudinal supply subset and the capacitive contacts C1 and C2 in the longitudinal sensing subset, or the capacitive contacts C1 and C4 in the longitudinal supply subset and the capacitive contacts C2 and C3 in the longitudinal sensing subset. In an embodiment, no contact C1-C4 is included in both the supply and longitudinal sensing subset of capacitive contacts C1-C4. The current that is supplied through the longitudinal supply subset of the capacitive contacts C1-C4 may be an alternating current.

The relatively close proximity of the capacitive contacts C1-C4 to the buried conducting layer 114 in the sample under test 102 may form capacitive coupling between the capacitive contacts C1-C4 and the buried conducting layer 114. The alternating current supplied to the sample under test 102 by the longitudinal supply subset of capacitive contacts C1-C4 may at least partially flow in a region of the semiconductor or insulator body 112 between the buried conducting layer 114 and the exposed surface 110, and between the capacitive contacts C1-C4 in the longitudinal supply subset (e.g., the capacitive contacts C1 and C2). At least some of this current may flow in a portion of the semiconductor or insulator body 112 that is opposite of the region under test 218 in the probe assembly 100.

The openings 216 (shown in FIG. 2) in the gate 208 (shown in FIG. 2) permit the current supplied to the longitudinal supply subset of capacitive contacts C1-C4 to flow through the undepleted portion of the semiconductor or insulator body 112. For example, the absence of the gate 208 which defines the openings 216 can cause portions of the semiconductor or insulator body 112 that oppose the openings 216 to not be depleted of electrons. Consequently, current may be able to more easily flow through the portions of the semiconductor or insulator body 112 that face or oppose the openings 216 (relative to portions of the semiconductor or insulator body 112 that face or oppose the gate 208. Due to the capacitive coupling of the capacitive contacts C1-C4 in the longitudinal sensing subset (e.g., the capacitive contacts C3 and C4) with the buried conducting layer 114, a voltage may be induced in the capacitive contacts C1-C4 of the longitudinal sensing subset. This induced voltage can be sensed by the controller 202 via the conductive bodies 204. The openings 216 also permit this induced voltage to be sensed by the longitudinal sensing subset of the capacitive contacts C1-C4.

The induced voltage that is sensed by the controller 202 between the capacitive contacts C1-C4 in the longitudinal sensing subset may be used to determine the sheet resistance ($R_S$) of the undepleted portion of the sample under test 102 (e.g., the portion of the sample under test 102 that opposes the region under test 218 of the probe assembly 100). For example, a longitudinal resistance ($R_L$) may be calculated from the sensed voltage (V) and the current supplied to the longitudinal supply subset of capacitive contacts C1-C4 as follows:

$$R_L = \frac{V}{I} \qquad \text{(Equation \#1)}$$

In order to determine the sheet resistance ($R_S$), the longitudinal resistance ($R_L$) may need to be modified by a geometric scaling factor. The geometric scaling factor may change based on the shape of the sample under test 102. For a planar square sample under test 102, the sheet resistance ($R_S$) may be determined from the longitudinal resistance ($R_L$) as follows:

$$R_S = \frac{\pi}{\log(2)} \times R_L \qquad \text{(Equation \#2)}$$

In Equation #2, $$\frac{\pi}{\log(2)}$$

represents the geometric scaling factor for the planar square sample under test 102. Other geometric scaling factors may be used with differently shaped samples under test 102.

To measure the Hall resistance ($R_H$), the probe assembly 100 is brought into contact or close proximity with the sample under test 102 or remains into contact or close proximity with the sample under test 102, as described above. Although the system 200 is described as measuring the sheet resistance before the Hall resistance, alternatively, the Hall resistance may be measured before the sheet resistance, only the sheet resistance may be measured, or only the Hall resistance may be measured.

Similar to measuring the sheet resistance, the controller 202 directs one or more power sources 206 to supply a negative voltage to the gate 208 via one or more of the conductive bodies 204. This voltage may be a direct current voltage. The negative voltage may be sufficiently large such that electrons in portions of the sample under test 102 that face the gate 208 are depleted semiconductor or insulator body 112 in the buried conducting layer 114. The electrons may be depleted in regions of the buried conducting layer 114 that are opposite the outer periphery portion 214, the separation fingers 210, and/or the lateral extensions 212 of the gate 208.

The sample under test 102 (or at least the portion of the sample under test 102 that is being examined by the probe assembly 100) is placed within a magnetic field (B). This magnetic field may be provided by one or more magnets 404. As shown in FIG. 4, the magnet 404 may be disposed on a side of the sample under test 102 that is opposite of the location of the probe assembly 100. Alternatively, the magnet 404 may be positioned elsewhere. The magnet 404 may include a permanent magnet, electromagnet, or other magnet. As shown in FIG. 4, the magnetic field is oriented perpendicular or substantially perpendicular to the exposed surface 110 of the sample under test 102. In an embodiment, the sample under test 102 may or may not be exposed to the magnetic field when the neighboring capacitive contacts C1-C4 inject a current into the sample under test 102 and the other neighboring capacitive contacts C1-C4 sense the voltage response, but is exposed to the magnetic field when the non-neighboring capacitive contacts C1-C4 inject a current into the sample under test 102 and the other non-neighboring capacitive contacts C1-C4 sense the voltage response.

The controller 202 supplies electric current to a third subset of the capacitive contacts C1-C4 and measures the voltage response, or induced voltage, in a fourth, different subset of the capacitive contacts C1-C4 while the sample under test 102 is exposed to the magnetic field. The third subset of capacitive contacts C1-C4 through which the current is supplied may be referred to as a transverse supply subset of the capacitive contacts C1-C4 and the fourth subset of capacitive contacts C1-C4 through which the voltage response is measured may be referred to as a transverse sensing subset of the capacitive contacts C1-C4.

The capacitive contacts C1-C4 in the transverse supply subset may be non-neighboring capacitive contacts C1-C4 or capacitive contacts C1-C4 that are not adjacent to each other. The capacitive contacts C1-C4 in the transverse supply subset may be separated from each other by another contact C1-C4 that is not included in the transverse supply subset of the capacitive contacts C1-C4. For example, the capacitive contacts C1-C4 in the transverse supply subset may be the capacitive contacts C1 and C3. The capacitive contacts C1-C4 in the transverse sensing subset may be the other non-neighboring capacitive contacts, such as the capacitive contacts C2 and C4. In the embodiment illustrated in FIG. 2, the capacitive contacts C1-C4 in each of the transverse supply subset and the transverse sensing subset are diagonal from each other. Alternatively, other pairs of separated capacitive contacts C1-C4 may be included in the transverse supply and sensing subsets, such as the capacitive contacts C2 and C4 being in the transverse supply subset and the capacitive contacts C1 and C3 in the transverse sensing subset.

The current that is supplied through the transverse supply subset of the capacitive contacts C1-C4 may be an alternating current. The relatively close proximity of the capacitive contacts C1-C4 to the buried conducting layer 114 in the sample under test 102 may form capacitive coupling between the capacitive contacts C1-C4 and the buried conducting layer 114. The alternating current supplied to the sample under test 102 by the transverse supply subset of capacitive contacts C1-C4 may at least partially flow in a region of the semiconductor or insulator body 112 between the buried conducting layer 114 and the exposed surface 110, and between the capacitive contacts C1-C4 in the transverse supply subset (e.g., the capacitive contacts C1 and C3). At least some of this current may flow in a portion of the semiconductor or insulator body 112 that is opposite of the region under test 218 in the probe assembly 100. Due to the capacitive coupling of the capacitive contacts C1-C4 in the transverse sensing subset (e.g., the capacitive contacts C2 and C4) with the buried conducting layer 114, a voltage may be induced in the capacitive contacts C1-C4 of the transverse sensing subset. This induced voltage can be sensed by the controller 202 via the conductive bodies 204.

The induced voltage that is sensed by the controller 202 between the capacitive contacts C1-C4 in the transverse sensing subset may be used to determine the Hall resistance ($R_H$) of the undepleted portion of the sample under test 102 (e.g., the portion of the sample under test 102 that opposes the region under test 218 of the probe assembly 100). For example, a transverse Hall resistance ($R_H$) may be calculated from the sensed voltage (V) and the current supplied to the transverse supply subset of capacitive contacts C1-C4 as follows:

$$R_H = \frac{V}{I} \qquad \text{(Equation \#3)}$$

Once the sheet resistance ($R_S$) and Hall resistance ($R_H$) are measured, one or more additional characteristics of the sample under test 102 may be determined. For example, a charge carrier density of the semiconductor or insulator body 112 may be calculated from the Hall resistance ($R_H$) as follows:

$$n = \frac{B}{R_H e} \qquad \text{(Equation \#4)}$$

where n represents the charge carrier density of the sample under test 102 (such as the two dimensional sheet charge carrier density per unit area), B represents the magnetic field to which the sample under test 102 is exposed, and e represents the electron charge.

A charge carrier mobility (μ) of the semiconductor or insulator body 112 may be calculated from the sheet resistance ($R_S$) as follows:

$$\mu = \frac{1}{n e R_S} \qquad \text{(Equation \#5)}$$

In an embodiment, the probe assembly 100 described herein can be used to provide for relatively high resolution measurements of electrical characteristics of the sample under test 102. For example, the overlay 108 of the probe assembly 100 may be relatively small, such as 16 square millimeters (or another small size). The region under test 218 also may be made relatively small to provide for increased resolution, as the size of the region under test 218 also may represent the area of the sample under test 102 being examined by the probe assembly 100. For example, the region under test 218 may be 2,500 square microns ($\mu m^2$), 10,000 square microns, or another size. Keeping the size of the device overlay 108 relatively small compared to the sample under test can permit the probe assembly 100 to be used to measure in more areas of the sample under test 102, such as in locations that are closer to the outer edges of the sample under test 102. Larger contact areas C1-C4 can permit the characterization system 200 to operate at lower frequencies (e.g., supply alternating currents at lower frequencies), such as 100 Hertz (Hz), 1,000 Hz, and the like.

In an embodiment, the probe assembly 100 can be used with a p-type buried conducting layer in the semiconductor or insulator body 112. For example, instead of a negative bias (e.g., a negative voltage) applied to the depletion gate of the probe assembly, a positive bias (e.g., positive voltage) can be applied to the depletion gate to deplete regions of the sample under test of holes. The sample under test may then be characterized as otherwise described herein.

Figure 5:
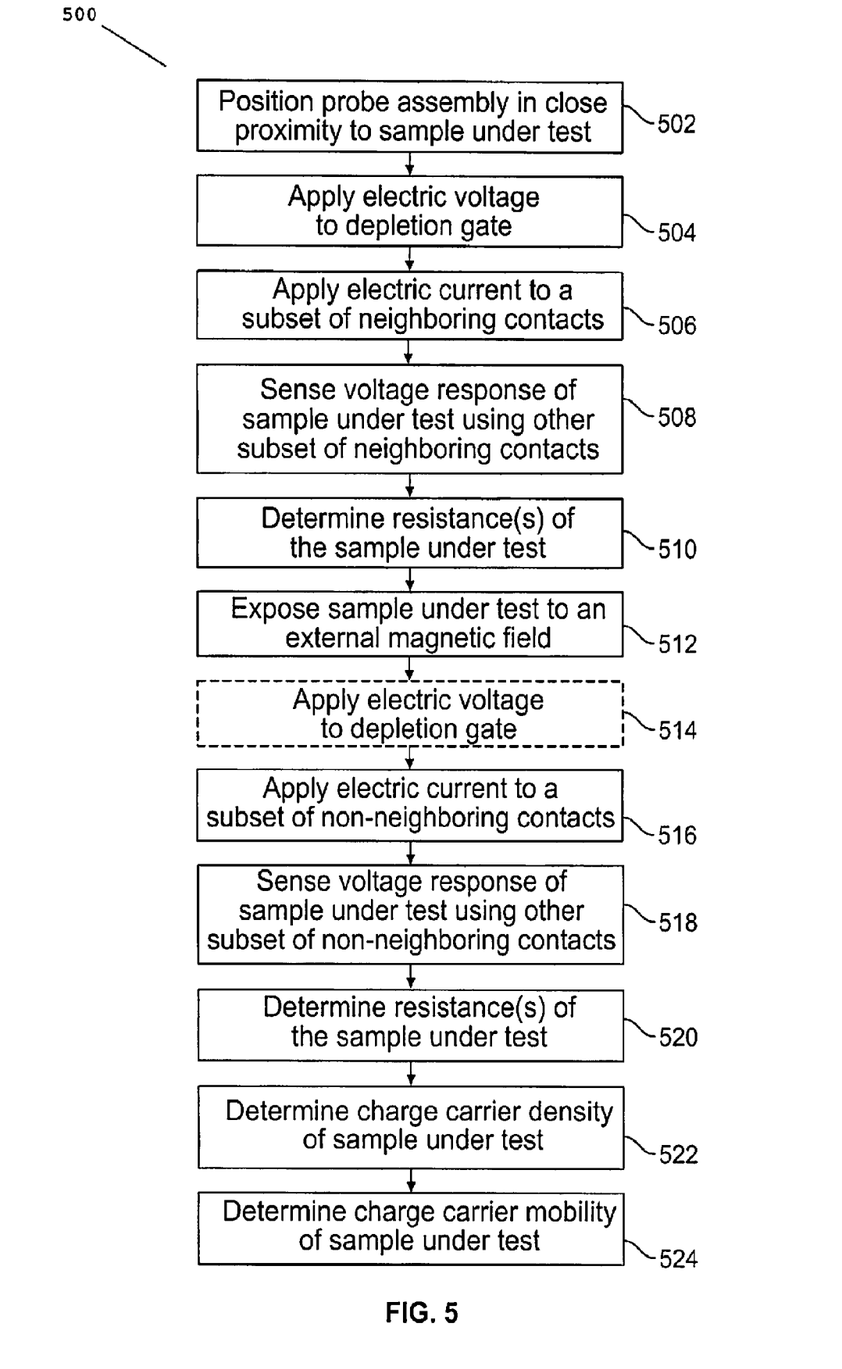
FIG. 5 is a flowchart of an example of a method for electrically characterizing a sample having a buried (e.g., non-exposed) conducting layer without contacting the conducting layer.

FIG. 5 is a flowchart of a method 500 for electrically characterizing a sample having a buried (e.g., non-exposed) conducting layer without contacting the conducting layer. The method 500 may be used in conjunction with the characterization system 200 described above and shown in FIG. 2.

At 502, a contactless probe assembly is placed in relatively close proximity to a sample under test. For example, the probe assembly 100 (shown in FIG. 1) may be placed onto the exposed surface 110 of the sample under test 102 such that the capacitive contacts C1-C4 of the probe assembly 100 engage the exposed surface 110. Alternatively, the probe assembly 100 may be positioned within a threshold distance of the buried conducting layer 114 of the sample under test 102, as described above.

The method 500 can be used to determine one or more electrical characteristics of the sample under test, such as a charge carrier mobility (μ), a charge carrier density (n), a sheet resistance ($R_S$), a Hall resistance ($R_H$), and the like. The operations described in connection with 504 through 524 may be performed in a different order than the order presented here.

At 504, a direct electric voltage is applied to a depletion gate of the probe assembly. For example, a negative direct voltage may be supplied to the gate 208 to deplete regions of semiconductor or insulator body 112 the buried conducting layer 114 of electrons. At 506, an alternating electric current is supplied to a subset of neighboring capacitive contacts of the probe assembly. For example, an alternating current may be supplied to the capacitive contacts C1, C2, to the capacitive contacts C2, C3, to the capacitive contacts C3, C4, or to the capacitive contacts C1, C4.

At 508, a voltage response of the semiconductor body (e.g., of the portion of the semiconductor body that opposes the region under test 218 of the probe assembly) to the current supplied to the neighboring capacitive contacts is sensed with the other neighboring capacitive contacts of the probe assembly. For example, the other two capacitive contacts of the probe assembly (other than the capacitive contacts that supplied the alternating current) may be capacitively coupled with the buried conducting layer and may be used to sense the voltage that is induced from the current supplied to the other capacitive contacts.

At 510, a resistance of the semiconductor body may be determined from the voltage response that is sensed at 508. For example, a longitudinal resistance may be calculated, as described above. A sheet resistance of the semiconductor body may be derived from this longitudinal resistance, such as by modifying the longitudinal resistance by a geometrical shaping factor At 512, the sample under test may be exposed to a magnetic field. The magnetic field may be an external magnetic field oriented perpendicular to the exposed surface of the sample under test, such as by orienting the north and south poles of the magnetic field opposite of each other and on opposite sides of the sample under test. One example of such a magnetic field is shown in FIG. 4.

At 514, a direct electric voltage is applied to a depletion gate of the probe assembly. For example, a negative direct voltage may be supplied to the gate 208 to deplete regions of semiconductor or insulator body 112 the buried conducting layer 114 of electrons. In an embodiment, the voltage that is applied to the depletion gate at 504 continues to be applied at 514 so that no additional or different voltage is applied at 514 (e.g., 514 is omitted). Alternatively, if the voltage applied to the depletion gate at 504 has been removed, then the same or different voltage may again be applied to the depletion gate at 514.

At 516, an electric current is supplied to non-neighboring capacitive contacts of the probe assembly. For example, an alternating current may be supplied to the capacitive contacts C1, C3 or to the capacitive contacts C2, C4. As described and shown above, these non-neighboring capacitive contacts may be on opposite sides of the region under test in the probe assembly, such as by being diagonal or other non-neighboring or non-adjacent positions.

At 518, a voltage response of the buried conducting layer 114 (e.g., of the portion of the semiconductor body that opposes the region under test 218 of the probe assembly) to the current supplied to the non-neighboring capacitive contacts is sensed with the other capacitive contacts of the probe assembly. For example, the other two capacitive contacts of the probe assembly (other than the capacitive contacts that supplied the alternating current) may be capacitively coupled with the buried conducting layer and may be used to sense the voltage that is induced from the current supplied to the other capacitive contacts.

At 520, a Hall resistance of the semiconductor body may be measured from the voltage response that is sensed at 520. At 522, a charge carrier density can be determined from the Hall resistance, as described above. At 524, a charge carrier mobility can be determined from the sheet resistance, and charge carrier density as described above.

In an embodiment, a probe assembly includes plural conductive capacitive contacts and a conductive depletion gate. The capacitive contacts are separate from each other. The depletion gate is disposed between and separates the capacitive contacts from each other. The depletion gate is configured to receive an electric voltage in order to deplete regions of a sample under test of electrons. The sample under test includes a semiconductor or insulator body having a buried conducting layer. In one aspect, the regions of the sample under test that are depleted of elections are located within the semiconductor or insulator body of the sample under test. The capacitive contacts are configured to be placed in close proximity to the buried conducting layer in the sample under test without engaging the buried conducting layer. A first subset of the capacitive contacts is configured to apply an alternating electric current to a portion of the sample under test and a second subset of the capacitive contacts is configured to sense an alternating voltage response of the portion of the sample under test in order to characterize one or more electrical properties of the sample under test without the capacitive contacts having ohmic contact with the buried conducting layer.

In one aspect, the first subset of the capacitive contacts is configured to apply the alternating electric current and the second subset of the capacitive contacts is configured to sense the alternating voltage response of the portion of the sample under test in order to determine at least one of a sheet resistance or a charge carrier mobility or a charge carrier density of the portion of the semiconductor or insulator sample under test.

In one aspect, the first subset of the capacitive contacts includes first and second neighboring capacitive contacts and the second subset of the capacitive contacts includes third and fourth neighboring capacitive contacts.

In one aspect, the first subset of the capacitive contacts is configured to apply the alternating electric current and the second subset of the capacitive contacts is configured to sense the alternating voltage response of the portion of the sample under test while the sample under test is exposed to a magnetic field oriented perpendicular to a surface of the sample under test that faces the capacitive contacts in order to determine at least one of a Hall resistance or a charge carrier density of the portion of the sample under test.

In one aspect, the first subset of the capacitive contacts includes non-neighboring first and third capacitive contacts and the second subset of the capacitive contacts includes non-neighboring second and fourth capacitive contacts.

In one aspect, the depletion gate includes separation fingers that extend between and separate the capacitive contacts from each other.

In one aspect, the depletion gate extends between the capacitive contacts and at least partially around a region under test between the capacitive contacts. The region under test represents an area that faces an undepleted region of the sample under test. For example, the undepleted region of the sample under test may include one or more portions of the semiconductor or insulator body, and/or the buried conducting layer, that is not depleted of all electrons. The depletion gate includes openings between the region under test and the capacitive contacts that permit the electric current applied by the first subset of capacitive contacts to be at least partially conducted through the undepleted region of the sample under test.

In one aspect, the depletion gate includes conductive fingers that extend between the capacitive contacts and separate the capacitive contacts from each other. The conductive fingers are defined by an outer width dimension. The capacitive contacts are in close proximity to the buried conducting layer when the capacitive contacts are separated from the buried conducting layer by a distance that is as small or smaller than the outer width dimension of the conductive fingers.

In an embodiment, a method (e.g., for electrically characterizing a sample under test that includes a semiconductor or insulator body with a buried conducting layer) includes positioning a probe assembly in close proximity to the buried conducting layer in the sample under test. The probe assembly has plural capacitive contacts that are separate from each other and a conductive depletion gate disposed between and separating the capacitive contacts from each other. The method also includes supplying the depletion gate with a direct electric voltage in order to deplete regions of the sample under test of electrons, conducting an alternating electric current through a first subset of the capacitive contacts to a portion of the sample under test, and sensing an alternating voltage response of the portion of the sample under test in response to the second alternating electric current being conducted through the first subset of the capacitive contacts in order to characterize one or more electrical properties of the sample under test without the capacitive contacts having ohmic contact with the buried conducting layer.

In one aspect, the method includes determining at least one of a sheet resistance or a charge carrier mobility of the portion of the sample under test using the alternating voltage response that is sensed.

In one aspect, the alternating electric current is conducted through first and second capacitive contacts that neighbor each other and the alternating voltage response is sensed using third and fourth capacitive contacts that neighbor each other.

In one aspect, the method includes exposing the sample under test to a magnetic field oriented perpendicular to a surface of the sample under test that faces the capacitive contacts. Determining at least one of a Hall resistance or a charge carrier density of the portion of the sample under test can be performed using the alternating voltage response that is sensed and the magnetic field.

In one aspect, the alternating electric current is conducted through non-neighboring first and third capacitive contacts and the voltage response is sensed using non-neighboring second and fourth capacitive contacts.

In one aspect, supplying the depletion gate with the first direct electric voltage depletes the regions of the sample under test of electrons between the capacitive contacts.

In an embodiment, a probe assembly includes capacitive contacts separated from each other and arranged around a region under test. The capacitive contacts are configured to be positioned proximate to a sample under test. The sample under test includes a semiconductor or insulator body having a buried conducting layer. The capacitive contacts are configured to be positioned proximate to the sample under test without contacting the buried conducting layer. A first subset of the capacitive contacts is configured to inject an alternating current into the sample under test outside of a portion of the sample under test that faces the region under test between the capacitive contacts. A different, second subset of the capacitive contacts is configured to sense an alternating voltage response of the portion of the sample under test in response to the alternating current being injected into the sample under test. The voltage response is indicative of at least one of a charge carrier mobility or a charge carrier density in the portion of the sample under test that faces the region under test.

In one aspect, the first subset of the capacitive contacts includes first and second neighboring capacitive contacts and the second subset of the capacitive contacts includes third and fourth neighboring capacitive contacts.

In one aspect, the first subset of the capacitive contacts includes first and second non-neighboring capacitive contacts and the second subset of the capacitive contacts includes third and fourth non-neighboring capacitive contacts.

In one aspect, the third and fourth non-neighboring capacitive contacts are configured to sense the voltage response when the sample under test is exposed to a magnetic field oriented perpendicular to a surface of the sample under test that faces the capacitive contacts. The voltage response is representative of a Hall resistance of the portion of the sample under test.

In one aspect, the probe assembly also includes one or more conductive depletion gates extending between the capacitive contacts and at least partially extending around a periphery of the region under test. The one or more depletion gates are configured to receive a direct voltage to deplete portions of the sample under test that face the one or more depletion gates of electrons.

In one aspect, the one or more depletion gates define openings between the capacitive contacts and the region under test.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the inventive subject matter without departing from its scope. While relative dimensions described and/or shown herein are intended to define the parameters of the inventive subject matter, they are by no means limiting and are example embodiments. Many other embodiments will be apparent to one of ordinary skill in the art upon reviewing the above description. The scope of the inventive subject matter should, therefore, be determined with reference to the appended clauses, along with the full scope of equivalents to which such clauses are entitled. In the appended clauses, the terms "including" and "in which" are used as the plain-English equivalents of the respective terms "comprising" and "wherein." Moreover, in the following clauses, the terms "first," "second," and "third," etc. are used merely as labels, and are not intended to impose numerical requirements on their objects. Further, the limitations of the following clauses are not written in means-plus-function format and are not intended to be interpreted based on 35 U.S.C. §112, sixth paragraph, unless and until such clause limitations expressly use the phrase "means for" followed by a statement of function void of further structure.

The foregoing description of certain embodiments of the inventive subject matter will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (for example, processors or memories) may be implemented in a single piece of hardware (for example, a general purpose signal processor, microcontroller, random access memory, hard disk, and the like). The various embodiments are not limited to the arrangements and instrumentality shown in the drawings.

The invention claimed is:

1. A probe assembly comprising:
   plural conductive capacitive contacts that are separate from each other; and
   a conductive depletion gate disposed between and separating the capacitive contacts from each other, the depletion gate configured to receive an electric voltage in order to deplete regions of a sample under test of electrons, the sample under test includes a semiconductor or insulator body having a buried conducting layer,
   wherein the capacitive contacts are configured to be placed in close proximity to the buried conducting layer in the sample under test without engaging the buried conducting layer, a first subset of the capacitive contacts configured to apply an alternating electric current to a portion of the sample under test and a second subset of the capacitive contacts configured to sense an alternating voltage response of the portion of the sample under test in order to characterize one or more electrical properties of the sample under test without the capacitive contacts having ohmic contact with the buried conducting layer.

2. The probe assembly of claim 1, wherein the first subset of the capacitive contacts is configured to apply the alternating electric current and the second subset of the capacitive contacts is configured to sense the alternating voltage response of the portion of the sample under test in order to determine at least one of a sheet resistance or a charge carrier mobility or a charge carrier density of the portion of the semiconductor or insulator sample under test.

3. The probe assembly of claim 2, wherein the first subset of the capacitive contacts includes first and second neighboring capacitive contacts and the second subset of the capacitive contacts includes third and fourth neighboring capacitive contacts.

4. The probe assembly of claim 1, wherein the first subset of the capacitive contacts is configured to apply the alternating electric current and the second subset of the capacitive contacts is configured to sense the alternating voltage response of the portion of the sample under test while the sample under test is exposed to a magnetic field oriented perpendicular to a surface of the sample under test that faces the capacitive contacts in order to determine at least one of a Hall resistance or a charge carrier density of the portion of the sample under test.

5. The probe assembly of claim 4, wherein the first subset of the capacitive contacts includes non-neighboring first and third capacitive contacts and the second subset of the capacitive contacts includes non-neighboring second and fourth capacitive contacts.

6. The probe assembly of claim 1, wherein the depletion gate includes separation fingers that extend between and separate the capacitive contacts from each other.

7. The probe assembly of claim 1, wherein the depletion gate extends between the capacitive contacts and at least partially around a region under test between the capacitive contacts, the region under test representing an area that faces an undepleted region of the sample under test, the depletion gate including openings between the region under test and the capacitive contacts that permit the electric current applied by the first subset of capacitive contacts to be at least partially conducted through the undepleted region of the sample under test.

8. The probe assembly of claim 1, wherein the depletion gate includes conductive fingers that extend between the capacitive contacts and separate the capacitive contacts from each other, the conductive fingers defined by an outer width dimension, wherein the capacitive contacts are in close proximity to the buried conducting layer when the capacitive contacts are separated from the buried conducting layer by a distance that is as small or smaller than the outer width dimension of the conductive fingers.

9. A method comprising:
positioning a probe assembly in close proximity to a buried conducting layer in a sample under test, the probe assembly having plural conductive capacitive contacts that are separate from each other and a conductive depletion gate disposed between and separating the capacitive contacts from each other, the sample under test including a semiconductor or insulator body having a buried conducting layer;
supplying the depletion gate with a direct electric voltage in order to deplete regions of the sample under test of electrons;
conducting an alternating electric current through a first subset of the capacitive contacts to a portion of the sample under test; and
sensing an alternating voltage response of the portion of the sample under test in response to the second alternating electric current being conducted through the first subset of the capacitive contacts in order to characterize one or more electrical properties of the sample under test without the contacts having ohmic contact with the buried conducting layer.

10. The method of claim 9, further comprising determining at least one of a sheet resistance or a charge carrier mobility of the portion of the sample under test using the alternating voltage response that is sensed.

11. The method of claim 10, wherein the alternating electric current is conducted through first and second capacitive contacts that neighbor each other and the alternating voltage response is sensed using third and fourth capacitive contacts that neighbor each other.

12. The method of claim 9, further comprising exposing the sample under test to a magnetic field oriented perpendicular to a surface of the sample under test that faces the capacitive contacts, wherein determining at least one of a Hall resistance or a charge carrier density of the portion of the sample under test using the alternating voltage response that is sensed and the magnetic field.

13. The method of claim 12, wherein the alternating electric current is conducted through non-neighboring first and third capacitive contacts and the voltage response is sensed using non-neighboring second and fourth capacitive contacts.

14. The method of claim 9, wherein supplying the depletion gate with the first direct electric voltage depletes the regions of the sample under test of electrons between the capacitive contacts.

15. A probe assembly comprising:
conductive capacitive contacts separated from each other and arranged around a region under test, the contacts configured to be positioned proximate to a sample under test, the sample under test including a semiconductor or insulator body having a buried conducting layer, the capacitive contacts configured to be positioned proximate to the sample under test without contacting the buried conducting layer,
wherein a first subset of the capacitive contacts is configured to inject an alternating current into the sample under test outside of a portion of the sample under test that faces the region under test between the capacitive contacts, and
wherein a different, second subset of the capacitive contacts is configured to sense an alternating voltage response of the portion of the sample under test in response to the alternating current being injected into the sample under test, the voltage response indicative of at least one of a charge carrier mobility or a charge carrier density in the portion of the sample under test that faces the region under test.

16. The probe assembly of claim 15, wherein the first subset of the capacitive contacts includes first and second neighboring capacitive contacts and the second subset of the contacts includes third and fourth neighboring capacitive contacts.

17. The probe assembly of claim 15, wherein the first subset of the capacitive contacts includes first and second non-neighboring capacitive contacts and the second subset of the capacitive contacts includes third and fourth non-neighboring capacitive contacts.

18. The probe assembly of claim 17, wherein the third and fourth non-neighboring capacitive contacts are configured to sense the voltage response when the sample under test is exposed to a magnetic field oriented perpendicular to a surface of the sample under test that faces the capacitive contacts, the voltage response being representative of a Hall resistance of the portion of the sample under test.

19. The probe assembly of claim 15, further comprising one or more conductive depletion gates extending between the capacitive contacts and at least partially extending around a periphery of the region under test, the one or more depletion gates configured to receive a direct voltage to deplete portions of the sample under test that face the one or more depletion gates of electrons.

20. The probe assembly of claim 19, wherein the one or more depletion gates define openings between the capacitive contacts and the region under test.

* * * * *